(12) United States Patent
Gless, Jr. et al.

(10) Patent No.: US 8,853,201 B2
(45) Date of Patent: Oct. 7, 2014

(54) SULFATE ESTERS OF NORIBOGAINE

(71) Applicant: DemeRx, Inc., Miami, FL (US)

(72) Inventors: Richard D. Gless, Jr., Oakland, CA (US); Robert M. Moriarty, Michiana Shores, IN (US)

(73) Assignee: DemeRx, Inc., Ft. Lauderdale, FL (US)

( * ) Notice: Subject to any disclaimer, the term of this patent is extended or adjusted under 35 U.S.C. 154(b) by 152 days.

(21) Appl. No.: 13/708,844

(22) Filed: Dec. 7, 2012

(65) Prior Publication Data

US 2013/0165425 A1 Jun. 27, 2013

Related U.S. Application Data

(60) Provisional application No. 61/569,144, filed on Dec. 9, 2011.

(51) Int. Cl.
| | |
|---|---|
| *A61K 31/55* | (2006.01) |
| *C07D 487/22* | (2006.01) |
| *C07D 471/18* | (2006.01) |

(52) U.S. Cl.
CPC ............ *C07D 487/22* (2013.01); *C07D 471/18* (2013.01)
USPC ..................................... 514/214.02; 540/579

(58) Field of Classification Search
USPC ...................................... 514/214.02; 540/579
See application file for complete search history.

(56) References Cited

U.S. PATENT DOCUMENTS

| | | | |
|---|---|---|---|
| 2,813,873 A | 11/1957 | Janot et al. |
| 4,626,539 A | 12/1986 | Aungst et al. |
| 4,806,341 A | 2/1989 | Chien et al. |
| 5,149,538 A | 9/1992 | Granger et al. |
| 5,616,575 A | 4/1997 | Efange et al. |
| 6,211,360 B1 | 4/2001 | Glick et al. |
| 6,348,456 B1 | 2/2002 | Mash et al. |
| 7,220,737 B1 | 5/2007 | Mash |

OTHER PUBLICATIONS

Bloomer, et al., "Arc/Arg3.1 Translation Is Controlled by Convergent N-Methyl-D-aspartate and Gs-coupled Receptor Signaling Pathways," J.Biol. Chem., (2008), 283(1):582-592.
Huffman, et al., "A formal Synthesis of (±)-Ibogamine," J. Org. Chem., (1985), 50:1460-1464.
International Search Report and Written Opinion dated Mar. 11, 2013 in related PCT Application No. PCT/US2012/067627.
Suvarna, et al., "Hydrolysis of N-Methly-D-aspartate Receptor-Stimulated cAMP and cGMP by PDE4 and PDE2 Phosphodiesterases in Primary Neuronal Cultures of Rat Cerebral Cortex and Hippocampus," Journal of Pharmacology and Experimental Therapeutics, (2002), 302:249-256.

*Primary Examiner* — Brenda Coleman
(74) *Attorney, Agent, or Firm* — Foley & Lardner LLP

(57) ABSTRACT

Disclosed herein are sulfate esters of noribogaine or 9,17 dihydronoribogaine, and pharmaceutically acceptable salts of each thereof, pharmaceutical compositions comprising such compounds, and methods of their use, including in treating addiction and/or pain.

8 Claims, No Drawings

SULFATE ESTERS OF NORIBOGAINE

CROSS-REFERENCE TO RELATED APPLICATION

This application claims the benefit under 35 U.S.C. §119 (e) of U.S. Provisional Application Nos. 61/569,144, filed Dec. 9, 2011, which is incorporated herein by reference in its entirety.

FIELD OF THE INVENTION

This invention is directed to sulfate esters of noribogaine.

STATE OF THE ART

Noribogaine is a metabolite of ibogaine and is sometimes referred to as 12-hydroxyibogaine. U.S. Pat. No. 2,813,873 claims noribogaine albeit as "12-O-demethylibogaine" while providing an incorrect structural formula for ibogaine. Noribogaine can be depicted by the following formula:

Noribogaine and its pharmaceutically acceptable salts have recently received significant attention as a non-addictive alkaloid useful in treating drug dependency (U.S. Pat. No. 6,348,456) and as a potent analgesic (U.S. Pat. No. 7,220,737).

Noribogaine is typically administered orally or intravenously and becomes systemically available to the treated patient.

SUMMARY OF THE INVENTION

This invention is directed to sulfate esters of noribogaine and a vicinal dihydro derivative of noribogaine, and compositions comprising each of them. As used herein, the sulfate esters include pharmaceutically acceptable salts and esters (esterifying the OH group attached to the sulfur atom) thereof.

In one aspect of this invention is provided a compound of Formula I:

wherein:

⫽ refers to a single or a double bond provided that when ⫽ is a single bond, Formula I refers to the corresponding 9,17 dihydro compound;

R is hydrogen or $SO_2OR^2$;
$R^1$ is hydrogen or $SO_2OR^2$;
$R^2$ is hydrogen or $C_1$-$C_6$ alkyl;

provided that at least one of R and $R^1$ is not hydrogen; or a salt thereof.

As used herein, the 9,17 dihydro noribogaine sulfate ester derivatives include the 9α, 17β; 9α, 17α; 9β, 17α; and the 9β, 17β stereoisomers.

In one of its composition aspects, this invention provides for a pharmaceutical composition comprising a therapeutically effective amount of a compound of Formula I and at least a pharmaceutically acceptable excipient.

In one of its method aspects, this invention is directed to a method for treating pain in a patient, which method comprises administering to said patient a therapeutically effective amount of a compound of Formula I above optionally in the presence of at least a pharmaceutically acceptable excipient.

In another of its method aspects, this invention is directed to a method for treating addiction in a patient, which method comprises administering to said patient a therapeutically effective amount of a compound of Formula I above optionally in the presence of at least a pharmaceutically acceptable excipient.

DETAILED DESCRIPTION OF THE INVENTION

It is to be understood that this invention is not limited to particular embodiments described, as such may, of course, vary. It is also to be understood that the terminology used herein is for the purpose of describing particular embodiments only, and is not intended to be limiting, since the scope of this invention will be limited only by the appended claims.

It must be noted that as used herein and in the appended claims, the singular forms "a", "an", and "the" include plural referents unless the context clearly dictates otherwise. Thus, for example, reference to "a compound of Formula I" includes a plurality of compounds of Formula I such as a mixture of two or more of such compounds.

DEFINITIONS

Unless defined otherwise, all technical and scientific terms used herein have the same meaning as commonly understood by one of ordinary skill in the art to which this invention belongs. As used herein, the following terms have the following meanings As used herein, the term "comprising" or "comprises" shall mean that the compositions and methods include the recited elements, but not excluding others. "Consisting essentially of" when used to define compositions and methods, shall mean excluding other elements of any essential significance to the combination for the stated purpose. Thus, a composition or method consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

The term "about" when used before a numerical designation, e.g., temperature, time, amount, and concentration, including range, indicates approximations which may vary by (+) or (−) 10%, 5% or 1%.

As stated above, the invention is directed to the sulfate ester of noribogaine or a pharmaceutically acceptable salt thereof.

As used herein, the term "noribogaine" refers to the compound:

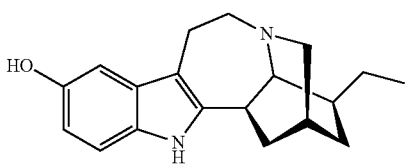

as well as its pharmaceutically acceptable salts thereof. Conventionally, noribogaine is prepared by demethylation of naturally occurring ibogaine:

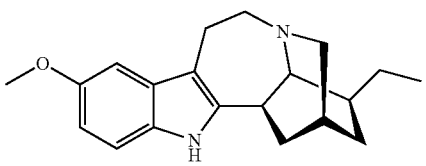

which is isolated from *Tabernanthe iboga*, a shrub of West Africa. Demethylation may be accomplished by conventional techniques such as by reaction with boron tribromide/methylene chloride at room temperature followed by conventional purification. (See, for example, Huffman, et al., J. Org. Chem. 50:1460 (1985)). This invention is not limited to any particular chemical form of noribogaine and the drug may be given to patients either as a free base or as a pharmaceutically acceptable addition salt.

As used herein, the term "alkyl" refers to alkyl groups having from 1 to 12 carbon atoms, preferably 1 to 6 carbon atoms and more preferably 1 to 3 carbon atoms. The alkyl group may contain linear or branched carbon chains. This term is exemplified by groups such as methyl, ethyl, n-propyl, iso-propyl, n-butyl, t-butyl, n-pentyl and the like. The term "$C_x$ alkyl" refers to an alkyl group having x carbon atoms, wherein x is an integer, for example, $C_3$ refers to an alkyl group having 3 carbon atoms.

As used herein, the term "cycloalkyl" refers to cyclic hydrocarbyl groups of from 3 to 10 carbon atoms having single or multiple cyclic rings including, by way of example, adamantyl, cyclopropyl, cyclobutyl, cyclopentyl, cyclooctyl and the like.

As used herein, the term "aryl" refers to an aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom.

As used herein, the term "heteroaryl" refers to an aromatic group of from 1 to 10 carbon atoms and 1 to 4 heteroatoms selected from the group consisting of oxygen, nitrogen, sulfur within the ring, wherein the nitrogen and/or sulfur atom(s) of the heteroaryl are optionally oxidized (e.g., N-oxide, —S(O)— or —S(O)$_2$—). Such heteroaryl groups can have a single ring (e.g., pyridyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. Examples of heteroaryls include pyridyl, pyrrolyl, indolyl, thiophenyl, and furyl.

As used herein, the terms "stress" or "anxiety" refer to the consequence when a patient fails to respond appropriately to emotional or physical threats, which may be actual or imagined. Stress symptoms or conditions may be cognitive, emotional, physical or behavioral, including, but not limited to a state of alarm and adrenaline production, short-term resistance as a coping mechanism, exhaustion, irritability, muscular tension, inability to concentrate, poor judgment, a general negative outlook, excessive worrying, moodiness, irritability, agitation, inability to relax, feeling lonely, isolated or depressed, aches and pains, diarrhea or constipation, nausea, dizziness, chest pain, headache, rapid heartbeat, eating too much or not enough, sleeping too much or not enough, social withdrawal, procrastination or neglect of responsibilities, increased alcohol, nicotine or drug consumption, and nervous habits such as pacing about or nail-biting. Stress can develop into a disabling disorder of excessive and irrational fears, such as obsessive-compulsive disorder, panic disorder, acute stress disorder and post traumatic stress disorder (PTSD).

As used herein, the term "protecting group" or "Pg" refers to well known functional groups which, when bound to a functional group, render the resulting protected functional group inert to the reaction to be conducted on other portions of the compound and the corresponding reaction condition, and which can be reacted to regenerate the original functionality under deprotection conditions. The identity of the protecting group is not critical and is selected to be compatible with the remainder of the molecule. In one embodiment, the protecting group is an "amino protecting group" which protects the amino functionality of noribogaine or derivatives thereof during the synthesis described here. Examples of amino protecting groups include, for instance, benzyl, acetyl, oxyacetyl, carbonyloxybenzyl (Cbz), and the like. In another embodiment, the protecting group is a "hydroxy protecting group" which protects the hydroxyl functionality of noribogaine or a derivative thereof during the synthesis described here. Examples of hydroxyl protecting groups include, for instance, benzyl, p-methoxybenzyl, p-nitrobenzyl, allyl, trityl, dialkylsilylethers, such as dimethylsilyl ether, and trialkylsilyl ethers such as trimethylsilyl ether, triethylsilyl ether, and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates such as methyl, ethyl, 2,2,2-trichloroethyl, allyl, and benzyl. Additional examples of amino and hydroxy protecting groups are found in standard reference works such as Greene and Wuts, Protective Groups in Organic Synthesis., 2d Ed., 1991, John Wiley & Sons, and McOmie Protective Groups in Organic Chemistry, 1975, Plenum Press. Methods for protecting and deprotecting the phenolic hydroxyl and indole N—H groups disclosed herein can be found in the art, and specifically in Greene and Wuts, supra, and the references cited therein.

As used herein, the term "pharmaceutically acceptable salt" refers to salts derived from organic or inorganic acids. Examples of such acids include, without limitation, hydrochloric acid, hydrobromic acid, phosphoric acid, sulfuric acid, methane sulfonic acid, phosphorous acid, nitric acid, perchloric acid, acetic acid, tartaric acid, lactic acid, succinic acid, citric acid, malic acid, maleic acid, aconitic acid, salicylic acid, thalic acid, embonic acid, enanthic acid, and the like.

As used herein, the term "therapeutically acceptable amount" refers to the amount of a composition of this invention that is sufficient to effect treatment, as defined herein, when administered to a subject in need of such treatment. The therapeutically effective amount will vary depending upon the subject and condition being treated, the weight and age of the subject, the severity of the condition, the particular composition or excipient chosen, the dosing regimen to be followed, timing of administration, the manner of administration and the like, all of which can be determined readily by one of ordinary skill in the art.

As used herein, the term "treatment" or "treating" means any treatment of a disease or condition in a patient, including:
preventing or protecting against the disease or condition, that is, causing the clinical symptoms not to develop, for example, in a subject at risk of suffering from such a disease or condition, thereby substantially averting onset of the disease or condition;
inhibiting the disease or condition, that is, arresting or suppressing the development of clinical symptoms; and/or
relieving the disease or condition, that is, causing the regression of clinical symptoms.

As used herein, the term "pain" refers to all types of pain, including neuropathic and nociceptive pain. It is also contemplated that the compositions disclosed herein can be used to treat other types of pain such as phantom pain which is the sensation of pain from a limb or organ that has been lost or from which a person no longer receives physical signals, and is an experience almost universally reported by amputees and quadriplegics.

As used herein, the term "addiction" refers to a persistent behavioral pattern marked by physical and/or psychological dependency to a substance, particularly drugs such as narcotics, stimulants, and sedatives, including but not limited to heroin, cocaine, alcohol, nicotine, caffeine, amphetamine, desoxyephedrine, methadone and combinations thereof. As used herein, the "treatment of addiction in a patient" refers to reducing the withdrawal symptoms associated with drug dependency as well as alleviating drug cravings in addicts. Such symptoms include nausea, vomiting, anxiety, abdominal cramps, muscle pain, chills and headache.

As used herein, the term "patient" or "subject" refers to mammals and includes humans and non-human mammals.

Compounds of the Invention

In one aspect of this invention is provided a compound of Formula I:

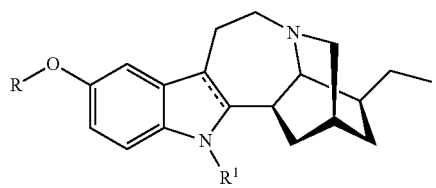

I wherein:

⟋⟋ refers to a single or a double bond provided that when

⟋⟋ is a single bond, Formula I refers to the corresponding dihydro compound;
R is hydrogen or $SO_2OR^2$;
$R^1$ is hydrogen or $SO_2OR^2$;
$R^2$ is hydrogen or $C_1$-$C_6$ alkyl;
provided that at least one of R and $R^1$ is not hydrogen; or a salt thereof.

In some embodiments, $R^1$ is hydrogen. In some embodiments, $R^1$ is $SO_2OR^2$. In some embodiments, R is hydrogen. In some embodiments, R is $SO_2OR^2$. In some embodiments, $R^2$ is hydrogen. In some embodiments, $R^2$ is $C_1$-$C_6$ alkyl. In some embodiments, ⟋⟋ is a double bond. In some embodiments, ⟋⟋ is a single bond.

In a preferred embodiment, this invention provides compounds of Formula I as tabulated below and pharmaceutically acceptable salts thereof.

| R | $R^1$ | $R^2$ | ⟋⟋ |
|---|---|---|---|
| $SO_2OR^2$ | hydrogen | hydrogen | double bond |
| $SO_2OR^2$ | hydrogen | hydrogen | single bond |
| hydrogen | $SO_2OR^2$ | hydrogen | double bond |
| hydrogen | $SO_2OR^2$ | hydrogen | single bond |
| $SO_2OR^2$ | $SO_2OR^2$ | hydrogen | double bond |
| $SO_2OR^2$ | $SO_2OR^2$ | hydrogen | Single bond |

Methods of the Invention

Noribogaine, has properties that are well suited to the treatment of pain and of withdrawal symptoms associated with drug dependency or abuse. In particular, it has been discovered that noribogaine binds to at least two classes of opioid receptors that have been associated with pain relief, the μ and κ receptors. In the case of the μ-type receptors, noribogaine acts as an opiate agonist. In addition, noribogaine elevates brain serotonin levels by blocking synaptic reuptake. It is believed that such levels (as well as ligand interactions at the μ and κ opiate receptors) play a role in the anxiety and drug cravings experienced by addicts during withdrawal. Noribogaine is the first μ opioid agonist which demonstrates analgesic properties without the propensity to cause addiction.

A sulfate of Formula I is a novel compound wherein the 12-hydroxyl group or the indole N—H of noribogaine is replaced with a biocompatible sulfate group. This sulfate group, including esters and/or salts thereof, exhibit enhanced solubility over noribogaine. In addition, the sulfate group will hydrolyze in the gastrointestinal tract in a manner which provides for a titrated release of noribogaine. The 9,17 dihydronoribogaine moiety is contemplated to be oxidized, over time, for example under aerobic conditions existing in vivo, to a double bond of noribogaine or a derivative thereof. As noribogaine has shown the potential for rapid absorption in the stomach, a titrated release of noribogaine is important in controlling the amount of noribogaine absorbed by the body over a unit period of time.

Treatment of Pain

Another aspect of this invention is directed to a method for treating pain in a patient. The pain can be any type of pain including, but not limited to neuropathic or nociceptive pain, and various types thereof including somatic, visceral and phantom pain. Accordingly, in one embodiment, the method comprises administering to said patient a pharmaceutical composition comprising a therapeutically effective amount of a compound of Formula I or a pharmaceutically acceptable salt thereof. See, for example, U.S. Pat. No. 7,220,737 (incorporated herein in its entirety by reference).

Treatment of Addiction

Noribogaine has been known to be used to treat patients for alleviating the symptoms associated with withdrawal from drug dependency. Accordingly, this invention is also directed to a method for treating addiction in a patient, which method comprises administering to said patient a pharmaceutical composition comprising a therapeutically effective amount of compound of Formula I or a pharmaceutically acceptable salt thereof. See, for example, U.S. Pat. No. 6,348,456 (incorporated herein in its entirety by reference).

In certain embodiments, the treatment of addiction in a patient comprises alleviating the symptoms associated with withdrawal from drug dependency. Such symptoms include nausea, vomiting, anxiety, abdominal cramps, muscle pain, chills and headache. In addition, noribogaine treatment decreases the drug cravings normally experienced by addicts after cessation of the self administration of the abused substance. It is contemplated that the compositions disclosed herein are especially useful in the treatment of addiction to narcotics such as heroin and methadone. However, it is also useful in treating patients addicted to cocaine, alcohol, amphetamines and combinations of these drugs.

Treatment of Stress

Stress can develop into a disabling disorder of excessive and irrational fears, such as obsessive-compulsive disorder, panic disorder, acute stress disorder and post traumatic stress disorder (PTSD). PTSD is a severe stress disorder that can develop after exposure to an event which results in psychological trauma. Such events usually involve death of someone else, threat of death to oneself or to someone else, or trauma to the physical, sexual, or psychological integrity of one's own or someone else. PTSD may be an acute stress response or a long term stress response to such an event when it overwhelms one's ability to cope. Symptoms of PTSD include some or all of the following: recurrent re-experiencing of the trauma, for example, intrusive, upsetting memories of the event, flashbacks of the traumatic events (acting or feeling like the event is happening again), recurring nightmares (either of the event or of other frightening things); feelings of intense distress and/or intense physical reactions when reminded of the trauma; avoidance to the point of having a phobia of places, people, and experiences that remind the sufferer of the trauma and a general numbing of emotional responsiveness; inability to remember important aspects of the trauma; and physical signs of hyperarousal, including sleep problems, trouble concentrating, irritability, anger, poor concentration, blackouts or difficulty remembering things, increased tendency and reaction to being startled, and hypervigilance to threat. Other symptoms include anhedonia, lack of interest in activities that used to be enjoyed, emotional deadness, distancing oneself from people, and/or a sense of a limited future (for example, not being able to think about the future or make future plans, not believing one will live much longer), guilt, shame, self-blame, depression and hopelessness, suicidal thoughts and feelings, feeling alienated and alone, headaches, stomach problems, chest pain and substance abuse.

It is contemplated that a composition comprising a compound of Formula I or a pharmaceutically acceptable salt thereof, either alone or in combination with an N-methyl D-aspartate pathway (NMDA) interrupter, will provide an effective treatment for stress. NMDA receptors belong to the glutamate receptor family. They are ligand-gated ion channels permeable to $Ca^{2+}$ and $Na^+$ ions, and are involved in synaptic plasticity, neuronal development, and learning and memory. Long-term potentiation, which is a cellular mechanism for memory, is regulated in part by NMDA receptor-mediated $Ca^{2+}$ influx. Activation of the NMDA receptor increases cAMP in the CA1 region of the hippocampus, which is mediated by $Ca^{2+}$-calmodulin-dependent adenylyl cyclase. The influx of $Ca^{2+}$ also stimulates $Ca^{2+}$-calmodulin-dependent nitric-oxide (NO) synthase (NOS) type to produce NO, which stimulates guanylyl cyclase to produce cGMP. cAMP and cGMP are involved in a number of intracellular processes such as activation of kinases, signal transduction, gene transcription, and regulation of channel function. Suvarna, et al., *J. Pharmacol. Exp. Ther.*, 302 (1):249-256 (2002). Further, NMDA signaling pathways also has regulatory effect on the Arc translation, which plays an important role in the consolidation of memory. Bloomer, et al., *J. Bio. Chem.* 283(1): 582-592 (2008). An N-methyl D-aspartate pathway interrupter can be an antagonist or inhibitor of any the receptors, enzymes, ion channels, etc. that are involved in the regulation of synaptic plasticity, neuronal development, and learning and memory in which NMDA receptors play a role.

In some embodiments, the NMDA pathway interrupter is selected from the group consisting of amantadine, dextromethorphan, dextrorphan, ethanol, ketamine, ketobemidone, memantine, methadone, nitrous oxide, phencyclidine, dizocilpine (MK801) and tramadol. In one embodiment, the NMDA pathway interrupter is cycloserine.

Dosage and Routes of Administration

It is contemplated that any route of administration and dosage form may be compatible with the compound and methods discussed above. The appropriate dosing regimen and route of administration can be readily determined by the attending clinician. In particular, a therapeutically effective amount of each of the components of the composition of this invention may be administered simultaneously or sequentially and in any order, and the components may be administered separately or as a fixed combination. The individual components of the composition can be administered separately at different times during the course of therapy or concurrently in divided or single composition forms.

Although compositions suitable for oral, intravenous or intraarterial delivery will probably be used most frequently, other routes that may be used include peroral, pulmonary, rectal, nasal, vaginal, lingual, intramuscular, intraperitoneal, intracutaneous and subcutaneous routes. In addition, it is contemplated that the composition can be administered transdermally in which drug is applied as part of a cream, gel, or patch (for examples of transdermal formulations, see U.S. Pat. Nos. 4,806,341; 5,149,538; and 4,626,539). Other dosage forms include tablets, capsules, pills, powders, aerosols, suppositories, parenterals, and oral liquids, including suspensions, solutions and emulsions. Sustained release dosage forms may also be used. All dosage forms may be prepared using methods that are standard in the art (see e.g., Remington's Pharmaceutical Sciences, 16th ed., A. Oslo editor, Easton Pa. 1980).

A compound of Formula I or an ester thereof, or a salt of each thereof can be used in conjunction with any of the vehicles and excipients commonly employed in pharmaceutical preparations, e.g., talc, gum arabic, lactose, starch, magnesium stearate, cocoa butter, aqueous or non-aqueous solvents, oils, paraffin derivatives, glycols, etc. Coloring and flavoring agents may also be added to preparations, particularly to those for oral administration. Solutions can be prepared using water or physiologically compatible organic solvents such as ethanol, 1,2-propylene glycol, polyglycols, dimethylsulfoxide, fatty alcohols, triglycerides, partial esters of glycerine and the like. Parenteral compositions containing noribogaine may be prepared using conventional techniques that may include sterile isotonic saline, water, 1,3-butanediol, ethanol, 1,2-propylene glycol, polyglycols mixed with water, Ringer's solution, etc.

It is contemplated that the dosage required for treating pain may differ from the dosage required for treating addiction, however, the dosing regimen can be readily determined by the attending clinician based on the desired treatment. It is contemplated that for the treatment of pain, the dosage of a compound of Formula I or an ester thereof, or a salt of each thereof administered to a patient may be from about 0.1 to about 100 mg per kg of body weight and, preferably, from about 0.1 to about 30 mg per kg of body weight. For the treatment of addiction, the dosage administered to a patient may be from about 0.1 to about 20 mg/ml.

Kit of Parts

One aspect of this invention is directed to a kit of parts comprising a composition as disclosed herein and a means for administering the composition to a patient in need thereof. The means for administration to a patient can include, for example, any one or combination of a syringe, a needle, an IV bag comprising the composition, a vial comprising the composition, etc.

Synthetic Methods

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, Protecting Groups in Organic Synthesis, Third Edition, Wiley, New York, 1999, and references cited therein.

Furthermore, the compounds of this invention will typically contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1 15 (John Wiley and Sons, 1991), Rodd's Chemistry of Carbon Compounds, Volumes 1 5 and Supplementals (Elsevier Science Publishers, 1989), Organic Reactions, Volumes 1 40 (John Wiley and Sons, 1991), March's Advanced Organic Chemistry, (John Wiley and Sons, 4th Edition), and Larock's Comprehensive Organic Transformations (VCH Publishers Inc., 1989).

Compounds of this invention may be prepared using noribogaine, which may be prepared according to known procedures, such as by demethylating ibogaine by methods known in the art, such as reaction with boron tribromide/methylene chloride at room temperature. Scheme 1, shows an exemplary general process for preparing compounds of this invention. Scheme 1 below shows reaction schemes for the sulfation of the 12-hydroxyl group and optionally for the disulfation of the 12-hydroxyl group and the indole nitrogen atom. Scheme 2 below shows reaction schemes for selective sulfation of the indole nitrogen atom by protecting the 12-hydroxyl group with a conventional hydroxyl protecting group. Scheme 2 follows much of the chemistry of Scheme 1 with the exception that a protecting group (Pg) is used to avoid sulfation of the 12 hydroxyl group. A variety of protecting groups, preferably those stable under acidic conditions are useful as the Pg, as will be apparent to the skilled artisan. An ester of the chlorosulfonic acid may be used to prepare an ester of the compound of Formula I. It is also contemplated that the indole nitrogen of noribogaine can be protected, the sulfation carried out on the hydroxy group of noribogaine, following which, the N-protecting group is deprotected. Methods for preparing the N-protected noribogaine will be apparent to the skilled artisan in view of this disclosure.

Scheme 1

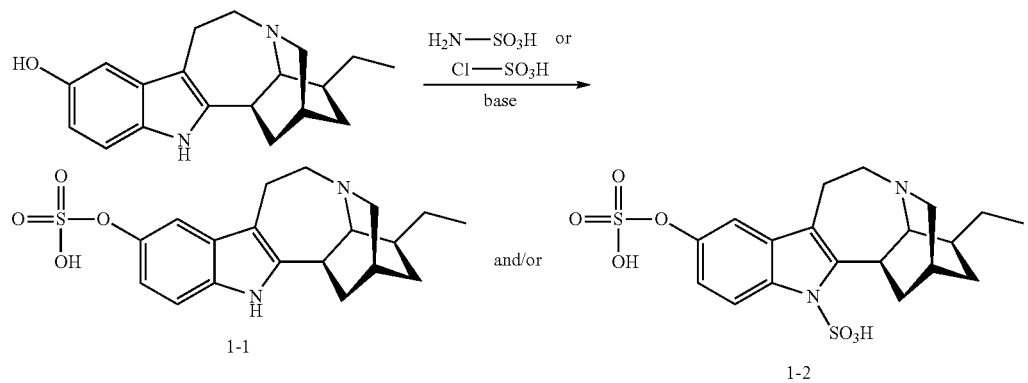

Scheme 2

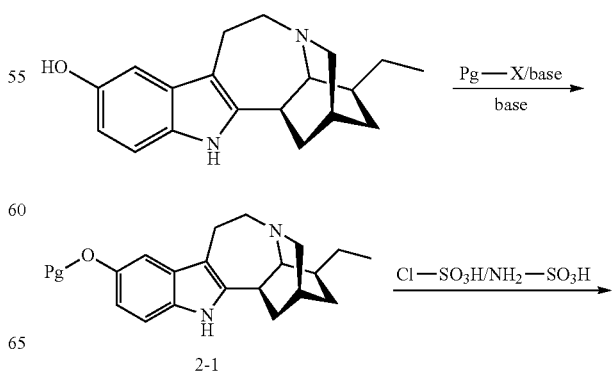

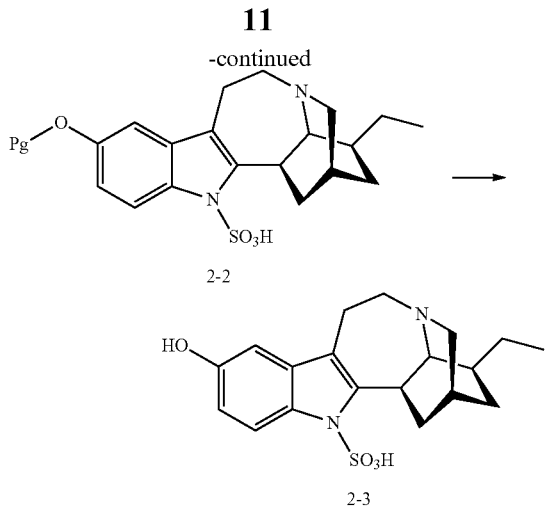

2-2

2-3

As shown above, X refers to a leaving group such a chloro, bromo, iodo, or a $R_s$—$SO_3$-moiety, where $R_s$ is $C_1$-$C_6$ alkyl optionally subtitued with 1-3 fluoro atoms or $R_s$ is phenyl optionally substituted with 1-3 halo or $C_1$-$C_6$ alkyl groups.

The dihydronoribogaine compounds of Formula I are synthesized by reducing the double bond of the corresponding noribogaine derivative. Various reducing agents well known to the skilled artisan are useful for this purpose. For example, catalytic hydrogenation employing hydrogen and a catalyst such as Pd/C or Pt/C is useful for providing the 9,17 cis, i.e. the α,α or the β,β dihydro compounds. Reagents such as borohydride or aluminum hydrides are useful for providing the α,β or the β,α dihydro compounds.

The reactions are carried out for a period of time sufficient to provide a substantial amount of the product, which can be ascertained by using routine methods such as thin layer chromatography, $^1$H-nuclear magnetic resonance (NMR) spectroscopy, and the likes. Compounds of Formula 1-1, 1-2, 2-1, 2-2, and 2-3 can be isolated and optionally purified using standard purification techniques, such as precipitation, crystallization, and/or liquid chromatography.

EXAMPLES

This invention is further defined by reference to the following examples. It will be apparent to those skilled in the art that many modifications, both to materials and methods, may be practiced without departing from the scope of the current invention.

| List of abbreviations and acronyms. | |
|---|---|
| Abbreviation | Meaning |
| HPLC | High Performace Liquid Chromatography |
| kg | Kilogram |
| m | Multiplet |
| M | Molar |
| M+ | Mass peak |
| Me | Methyl |
| mg | Milligram |
| MHz | Megahertz |
| mL | Milliliter |
| mM | Millimolar |
| mmol | Millimole |
| MS | Mass spectrometry |
| N | Normal |
| NMR | Nuclear magnetic resonance |
| prep | Preparative |

| List of abbreviations and acronyms. | |
|---|---|
| Abbreviation | Meaning |
| q.s. | Sufficient amount |
| r.t. | Room temperature |
| s | Singlet |
| t | Triplet |
| t-Bu | tert-Butyl |
| THF | Tetrahydrofuran |

Example 1

Formulations

The following ingredients are mixed intimately and pressed into single scored tablets.

| Ingredient | Quantity per tablet, mg |
|---|---|
| Sulfate Ester of Noribogaine | 40 |
| Cornstarch | 50 |
| Croscarmellose sodium | 25 |
| Lactose | 120 |
| Magnesium stearate | 5 |

The following ingredients are mixed intimately and loaded into a hard-shell gelatin

| Ingredient | Quantity per tablet, mg |
|---|---|
| Sulfate Ester of Noribogaine | 20 |
| Lactose, spray-dried | 148 |
| Magnesium stearate | 2 |

The following ingredients are mixed to form a suspension for oral administration (q.s.=sufficient amount).

| Ingredient | Amount | |
|---|---|---|
| Sulfate Ester of Noribogaine | 1.0 | g |
| Fumaric acid | 0.5 | g |
| Sodium chloride | 2.0 | g |
| Methyl paraben | 0.15 | g |
| Propyl paraben | 0.05 | g |
| Granulated sugar | 25.0 | g |
| Sorbitol (70% solution) | 13.0 | g |
| Veegum K (Vanderbilt Co) | 1.0 | g |
| Flavoring | 0.035 | mL |
| colorings | 0.5 | mg |
| distilled water | q.s. to 100 | mL |

The following ingredients are mixed to form an injectable formulation.

| Ingredient | Quantity per tablet, mg |
|---|---|
| Sulfate Ester of Noribogaine | 0.2 mg-20 mg |
| sodium acetate buffer solution, 0.4M | 2.0 mL |
| HCl (1N) or NaOH (1N) | q.s. to suitable pH |
| water (distilled, sterile) | q.s. to 20 mL |

A suppository of total weight 2.5 g is prepared by mixing the compound of the invention with Witepsol® H-15 (triglycerides of saturated vegetable fatty acid; Riches-Nelson, Inc., New York), and has the following composition:

| Ingredient | Quantity per tablet, mg |
|---|---|
| Sulfate Ester of Noribogaine | 500 mg |
| Witepsol ® H-15 | Balance |

Example 2

In Vivo Microdialysis in Adult Rats

A sulfate ester of noribogaine is given via a microdialysis probe in the right frontal cortex, while a probe in the left cortex can serve as a vehicle control site.

Guide cannulae (CMA/12 polyurethane, Carnegie Medicine, Sweden) is implanted into the left and right frontal (motor) cortex under anesthesia. The tips of the guide are positioned at coordinates according to Paxinos and Watson, The rat brain in stereotaxic coordinates, Sydney, Academic Press, 1986. Microdialysis experiments are performed following a recovery period of at least 3 days after surgery. The microdialysis probe is lowered through the guide cannula. 14 to 16 h after insertion, perfusion of the probe is started using Ringer solution (in mM 147 $Na^+$, 2.3 $Ca^{2+}$, 4.0 $K^+$ and 155.6 $Cl^-$, pH 6.0). Two dialysate samples are collected over a time period of 1 h before rats are injected with noribogaine. Following drug administration, further samples are collected over the next 2 h. The left microdialysis probe is perfused with the respective drug vehicle, e.g. Ringer solution.

Noribogaine concentrations in dialysate and plasma samples are by high performance liquid chromatography (HPLC) with UV detection.

Example 3

Treatment of PTSD

A 75 kg male patient presents with post traumatic stress disorder. The patient is treated with one of the pharmaceutical compositions of Example 1 with 10-100 mg of a NMDA receptor pathway interrupter as determined by the attending clinician. Administration is continued until the symptoms of post traumatic stress disorder are alleviated.

What is claimed is:

1. A compound of Formula I:

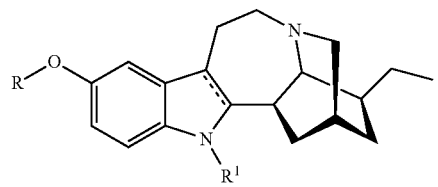

wherein:

⚌ refers to a single or a double bond provided that when ⚌ is a single bond, Formula I refers to the corresponding dihydro compound;

R is hydrogen or $SO_2OR^2$;
$R^1$ is hydrogen or $SO_2OR^2$;
$R^2$ is hydrogen or $C_1$-$C_6$ alkyl;
provided that at least one of R and $R^1$ is not hydrogen;
or a salt thereof.

2. The compound of claim 1, wherein $R^1$ is hydrogen.
3. The compound of claim 1, wherein $R^1$ is $SO_2OR^2$.
4. The compound of claim 1, wherein R is hydrogen.
5. The compound of claim 1, wherein R is $SO_2OR^2$.
6. A pharmaceutical composition comprising a compound of claim 1 and at least one pharmaceutically acceptable excipient.
7. A method for treating pain in a patient which method comprises administering to said patient a therapeutically effective amount of the compound of claim 1.
8. A method for treating addiction in a patient which method comprises administering to said patient a therapeutically effective amount of the compound of claim 1.

* * * * *